US00PP11498P

United States Patent [19]

Bloom

[11] Patent Number: Plant 11,498

[45] Date of Patent: Sep. 5, 2000

[54] CLEMATIS PLANT NAMED 'ALBLO'

[75] Inventor: Alan Bloom, Diss, United Kingdom

[73] Assignee: Blooms of Bressingham Ltd., Diss, United Kingdom

[21] Appl. No.: 09/129,434

[22] Filed: Aug. 5, 1998

[51] Int. Cl.[7] ..... A01H 5/00

[52] U.S. Cl. ..... Plt./228

[58] Field of Search ..... Plt./228

*Primary Examiner*—Howard J. Locker

*Assistant Examiner*—Kent L. Bell

*Attorney, Agent, or Firm*—C. A. Whealy

[57] ABSTRACT

A new and distinct cultivar of Clematis plant named 'Alblo', characterized by its upright and dense plant form; vigorous growth habit; dark green leaves; long flowering period; and numerous, showy lavender blue flowers.

1 Drawing Sheet

BACKGROUND OF THE INVENTION

The present invention relates to a new and distinct cultivar of Clematis, botanically known as *Clematis heracleifolia,* and hereinafter referred to by the cultivar name 'Alblo'. The new variety is being marketed under the name Alan Bloom.

The new Clematis is a naturally-occurring mutation of the *Clematis heracleifolia* cultivar 'Wyevale' (not patented). The new Clematis was discovered and selected by the Inventor as a single plant within a population of plants of the parent cultivar, the *Clematis heracleifolia* cultivar 'Wyevale', in a controlled environment in Bressingham, England, in 1990. The selection of this plant was based on its denser and more vigorous growth habit, and unique flower color.

Asexual reproduction of the new Clematis by divisions, basal cuttings, or by root cuttings taken in a controlled environment in Bressingham, England, has shown that the unique features of this new Clematis are stable and reproduced true to type in successive generations.

BRIEF SUMMARY OF THE INVENTION

Plants of the new Clematis have not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Alblo'. These characteristics in combination distinguish 'Alblo' as a new and distinct cultivar:

1. Upright and dense plant form.
2. Vigorous growth habit.
3. Dark green leaves.
4. Long flowering period.
5. Numerous, showy lavender blue flowers.

Plants of the new Clematis can be compared to plants of the parent cultivar 'Wyevale'. However, in side-by-side comparisons conducted in Bressingham, England, plants of the new Clematis differ from plants of the cultivar 'Wyevale' in the following characteristics:

1. Plants of the new Clematis have larger and darker green leaves than plants of the cultivar 'Wyevale'.

2. Plants of the new Clematis are more freely flowering than plants of the cultivar 'Wyevale'.

3. Plants of the new Clematis flower for a longer period of time than plants of the cultivar 'Wyevale'.

4. Flowers of plants of the new Clematis do not have a discernable fragrance whereas flowers of plants of the cultivar 'Wyevale' have a discernable fragrance.

5. Plants of the new Clematis have larger flowers and longer flower stems than plants of the cultivar 'Wyevale'.

6. Plants of the new Clematis have darker lavender blue flowers than plants of the cultivar 'Wyevale'.

A detailed comparison of plants of the cultivars 'Alblo' and 'Wyevale' appears in Chart A at the end of the specification.

BRIEF DESCRIPTION OF THE PHOTOGRAPH

The accompanying colored photograph illustrates the overall appearance of the new Clematis, showing the colors as true as it is reasonably possible to obtain in a colored reproduction of this type. The photograph comprises a top perspective view of typical plants of 'Alblo' in full flower. Flower and foliage colors in the photograph may appear different from the actual colors due to light reflectance.

DETAILED BOTANICAL DESCRIPTION

The aforementioned and following observations, measurements, values, and comparisons describe plants grown in Bressingham, England, in 7.5-liter containers under outdoor conditions which closely approximate commercial production conditions. During the one year growing season, day and night temperatures ranged form 6 to 27° C. and −6 to 10° C., respectively.

In the following description, color references are made to The Royal Horticultural Society Colour Chart except where general terms of ordinary dictionary significance are used.

Botanical classification: *Clematis heracleifolia* cultivar Alblo.

Parentage: Naturally-occurring mutation of *Clematis heracleifolia* cultivar 'Wyevale'.

Propagation:

*Type.*—By divisions, basal cuttings or by root cuttings.

*Time to develop roots.*—About 40 days during the late winter.

*Rooting habit.*—Fibrous.

Plant description:

*Plant form and growth habit.*—Perennial, herbaceous, dense, upright and clumping. Vigorous.

*Plant height, soil level to top of flowers.*—During one growing season plants will obtain a height of about 90 cm.

*Plant diameter, area of spread.*—During one growing season plants will obtain a width of about 40 cm.

*Internode length.*—About 8 cm.

*Stem color.*—147C.

*Stem texture.*—Pubescent.

Foliage description:

*Arrangement.*—Opposite; trifoliate.

*Leaf length.*—About 10 cm.

*Leaf width.*—About 11 cm.

*Terminal leaflet shape.*—Ovate with apiculate apex and attenuate base.

*Margin.*—Serrate.

*Texture.*—Rough, pubescence on both surfaces.

*Color.*—Mature foliage, upper surface: 147A. Mature foliage, lower surface: 147B.

*Petiole length.*—About 1.5 cm.

*Petiole color.*—96A.

Flower description:

*Natural flowering season.*—Flower initiation and development takes place from March to July, flowering occurs from July to September, about 50 days, when grown in Bressingham, England.

*Fragrance.*—None detected.

*Flower arrangement.*—Tubular single flowers arranged on spikes in short axillary clusters with about ten flowers and flower buds per cluster. Very freely flowering, about 380 flowers and flower buds per plant.

*Flower length.*—About 5 cm.

*Flower diameter.*—About 4.5 cm.

*Sepals.*—Appearance: Calyx consists of four petaloid sepals. Shape: Strap-shaped with acute apex; recurved at apex. Margin: Entire. Color: Fully opened, upper surface: 96A. Fully opened, lower surface: 96B.

*Flower stems* (*peduncle*).—Length: About 30 cm. Angle: Bent. Strength: Moderate. Color: 189A.

*Reproductive organs.*—Androecium: Stamen number: Numerous. Anther shape: Filiform. Anther size: About 2 mm. Anther color: Creamy yellow. Amount of pollen: Moderate. Pollen color: Yellow. Gynoecium: Pistil length: About 1.5 mm. Stigma shape: Obovate. Stigma color: Creamy yellow to white. Style length: About 5 mm. Style color: Creamy yellow to white. Ovary color: Gray to brown.

Disease resistance: No known Clematis diseases observed to date on plants grown under commercial conditions.

Seed production: Production of small dark brown seeds, encased in achenes, has been observed.

Temperature tolerance: Plants have been observed to tolerate temperatures down to −12° C. and high temperatures up to 28° C.

CHART A

| CHARACTERISTIC | 'ALBLO' | 'WYEVALE' |
|---|---|---|
| INTERNODE LENGTH | About 8 cm | About 6 cm |
| STEM COLOR | 147C | 148D |
| LEAF LENGTH | About 10 cm | About 8 cm |
| LEAF WIDTH | About 11 cm | About 9 cm |
| LEAF COLOR, UPPER SURFACE | 147A | 146C |
| LEAF COLOR, LOWER SURFACE | 147B | 146D |
| PETIOLE LENGTH | About 1.5 cm | About 1 cm |
| PETIOLE COLOR | 96A | 94C |
| QUANTITY OF FLOWERS AND FLOWER BUDS PER PLANT | About 380 | About 280 |
| FLOWERING PERIOD | About 50 days | About 40 days |
| FRAGRANCE | None | Present |
| FLOWER LENGTH | About 5 cm | About 3.5 cm |
| FLOWER DIAMETER | About 4.5 cm | About 2.5 cm |
| SEPAL COLOR, UPPER SURFACE | 96A | 94C |
| SEPAL COLOR, LOWER SURFACE | 96B | 94D |
| FLOWER STEM LENGTH | About 30 cm | About 25 cm |
| FLOWER STEM COLOR | 189A | 191B |

It is claimed:

1. A new and distinct Clematis plant named 'Alblo', as illustrated and described.

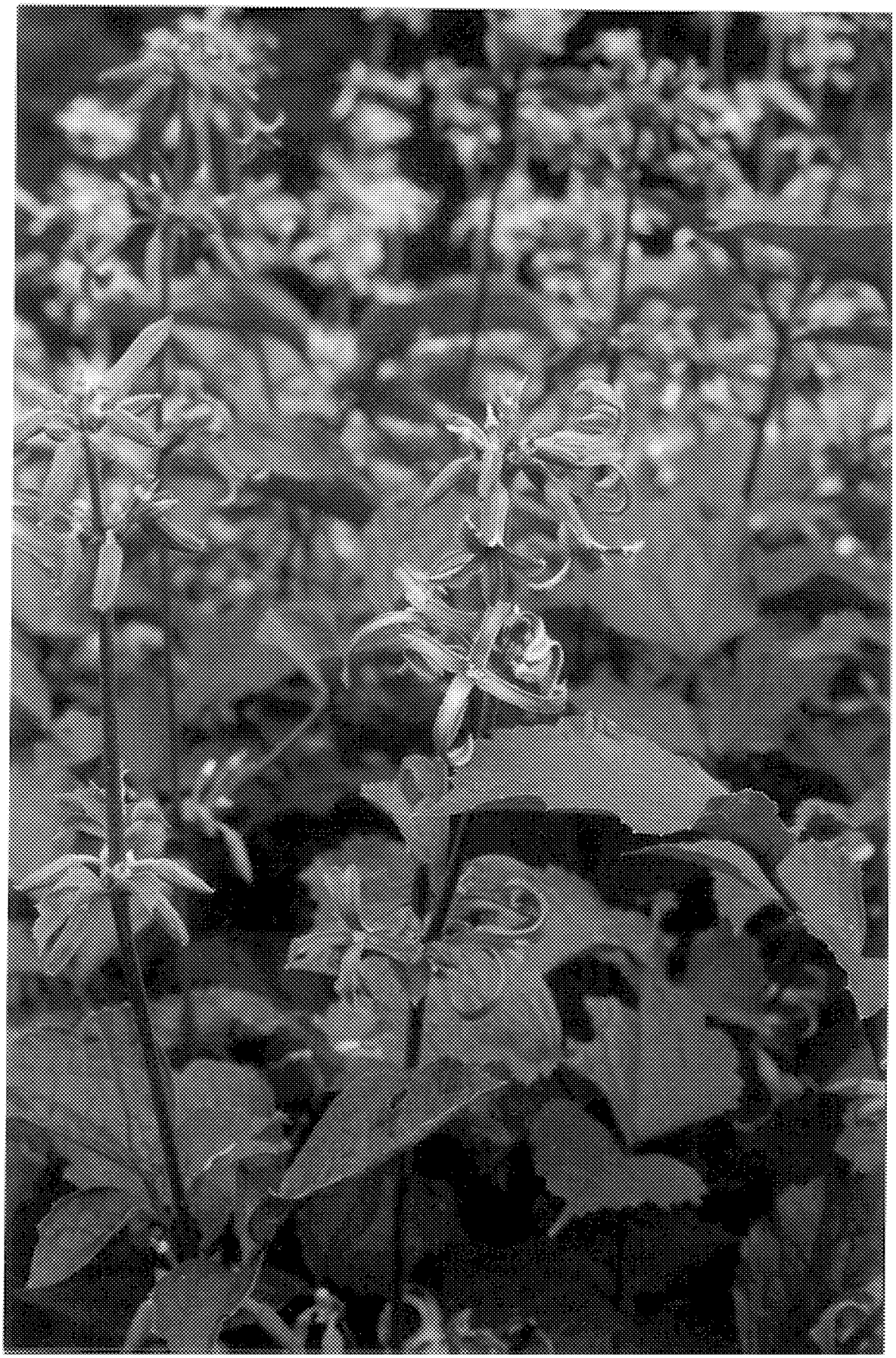

* * * * *